United States Patent
Hsieh et al.

(10) Patent No.: US 6,754,300 B2
(45) Date of Patent: Jun. 22, 2004

(54) METHODS AND APPARATUS FOR OPERATING A RADIATION SOURCE

(75) Inventors: Jiang Hsieh, Brookfield, WI (US); Samit K. Basu, Clifton Park, NY (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/064,189

(22) Filed: Jun. 20, 2002

(65) Prior Publication Data

US 2003/0235267 A1 Dec. 25, 2003

(51) Int. Cl.[7] ............................ H05G 1/60; G21K 3/00
(52) U.S. Cl. ............................ 378/16; 378/9; 378/159
(58) Field of Search ............................ 378/4, 7, 9, 16, 378/119, 121, 122, 124, 134, 159; 250/393

(56) References Cited

U.S. PATENT DOCUMENTS

| | | | |
|---|---|---|---|
| 4,682,291 A | 7/1987 | Reuveni ...................... 378/13 |
| 4,728,893 A | 3/1988 | Feinberg ...................... 324/312 |
| 5,396,889 A * | 3/1995 | Ueda et al. .................. 600/407 |
| 5,459,319 A | 10/1995 | Norsworthy ................. 250/349 |
| 5,488,421 A | 1/1996 | Hwang et al. .............. 348/448 |
| 5,530,731 A | 6/1996 | Polacin et al. ................. 378/15 |
| 5,663,995 A * | 9/1997 | Hu ............................... 378/15 |
| 5,778,046 A * | 7/1998 | Molloi et al. ................ 378/159 |
| 5,799,111 A | 8/1998 | Guissin ...................... 382/254 |
| 5,805,663 A * | 9/1998 | Mihara ...................... 378/98.2 |
| 5,809,178 A | 9/1998 | Anderson et al. ........... 382/251 |
| 5,818,896 A | 10/1998 | Hsieh .......................... 378/15 |
| 5,832,055 A | 11/1998 | Dewaele ...................... 378/62 |
| 6,069,979 A | 5/2000 | VanMetter ................... 382/260 |
| 6,069,982 A | 5/2000 | Reuman ..................... 382/275 |
| 6,138,093 A | 10/2000 | Ekudden et al. ............ 704/228 |
| 6,164,847 A | 12/2000 | Allen .......................... 400/74 |
| 6,215,115 B1 | 4/2001 | Baker et al. ................. 250/221 |
| 6,280,084 B1 * | 8/2001 | Toth ........................... 378/207 |
| 6,333,968 B1 * | 12/2001 | Whitlock et al. ........... 378/136 |
| 6,381,298 B2 | 4/2002 | Proksa et al. ................. 378/15 |

* cited by examiner

*Primary Examiner*—Edward J. Glick
*Assistant Examiner*—Allen C. Ho
(74) *Attorney, Agent, or Firm*—Carl B. Horton, Esq.; Armstrong Teasdale LLP

(57) ABSTRACT

A method for operating a radiation source includes providing a radiation source, providing a detector, and operating the radiation source and the detector such that the detector receives a substantially homogenous noise distribution.

24 Claims, 4 Drawing Sheets

ILLUSTRATION OF THE PRE-PATIENT FILTER TO MODIFY THE X-RAY FLUX

ILLUSTRATION OF TUBE CURRENT MODULATION APPROACH

ILLUSTRATION OF DWELL TIME MODULATION APPROACH

ILLUSTRATION OF UNEVENLY PACED X-RAY SPOTS

__US 6,754,300 B2__

METHODS AND APPARATUS FOR OPERATING A RADIATION SOURCE

BACKGROUND OF THE INVENTION

This invention relates generally to computed tomographic (CT) imaging, and more particularly to methods and apparatus for operating a CT radiation source.

Recently, many discussions have been centered on a CT scanning concept based on an inverted cone geometry. Using an inverted cone geometry, a large two-dimensional radiation source is used to cover nearly the entire scan field of view (FOV). A small detector is used to collect the radiation photons. One of the potential problems associated with using a non-point radiation source and a line radiation source is a noise in-homogeneity received by the detector.

SUMMARY OF THE INVENTION

In one aspect, a method for operating a radiation source is provided. The method includes providing a radiation source, providing a detector, and operating the radiation source and the detector such that the detector receives a substantially homogenous noise distribution.

In another aspect, a computer operating a radiation source installed on a scanning imaging system is provided. The imaging system includes a radiation source and a detector. The computer is programmed to operate the radiation source and the detector such that the detector receives a substantially homogenous noise distribution.

In a further aspect, a computed tomographic (CT) imaging system for operating a radiation source is provided. The CT system includes a radiation source, a detector array, and a computer coupled to the detector array and the radiation source. The computer is configured to operate the radiation source such that an inverted-cone beam geometry is received by the detector.

DETAILED DESCRIPTION

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a helical scan may be performed. To perform a helical scan, the patient is moved while the data for the prescribed number of slices is acquired. Such a system generates a single helix from a one fan beam helical scan. The helix mapped out by the fan beam yields projection data from which images in each prescribed slice may be reconstructed.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
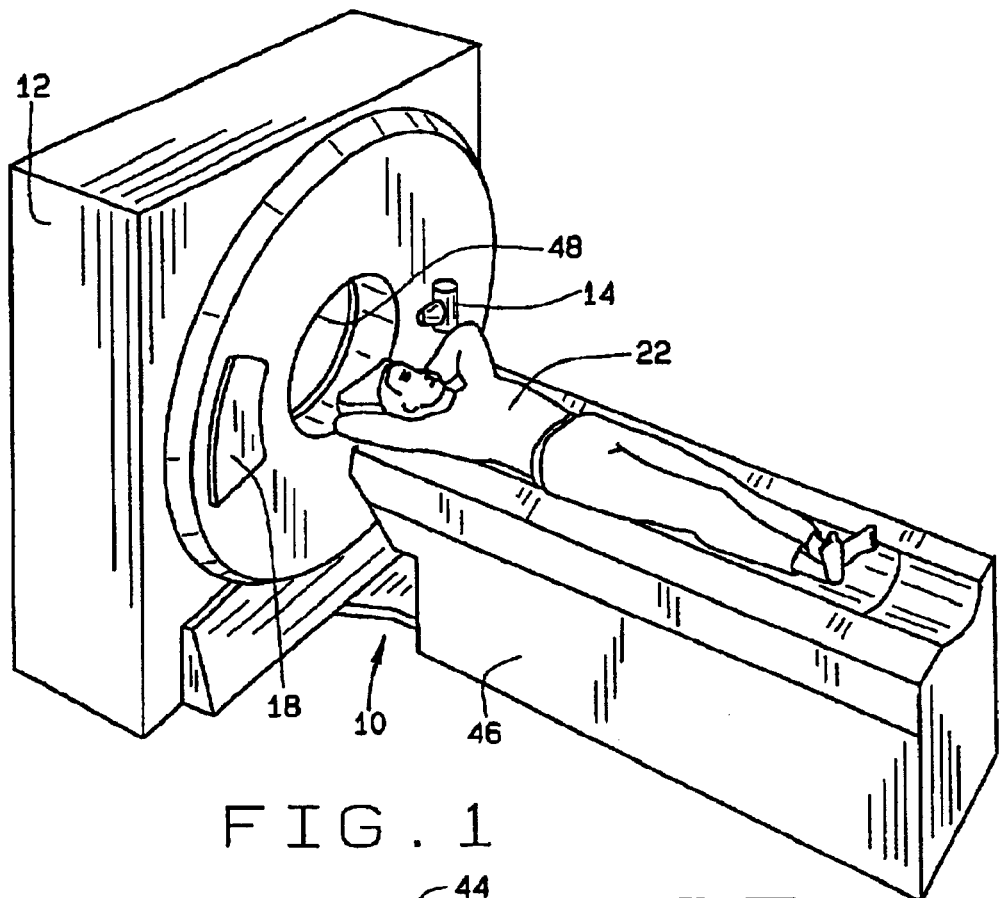
FIG. 1 is a pictorial view of a CT imaging system.

FIG. 1 is a pictorial view of a CT imaging system __10__. FIG. __2__ is a block schematic diagram of system __10__ illustrated in FIG. __1__. In the exemplary embodiment, a computed tomography (CT) imaging system __10__, is shown as including a gantry __12__ representative of a "third generation" CT imaging system. Gantry __12__ has a radiation source __14__ that projects a cone beam __16__ of X-rays toward a detector array __18__ on the opposite side of gantry __12__. In one embodiment, radiation source __14__ is a two-dimensional radiation source that projects a plurality of cone beams __16__ from a plurality of locations on radiation source __14__, also referred to herein as spots, on radiation source __14__, toward detector __18__ such that at least one of an inverted-cone beam geometry and a non-inverted cone beam geometry is received by detector __18__. another embodiment, radiation source __14__ is a line source.

Figure 2:
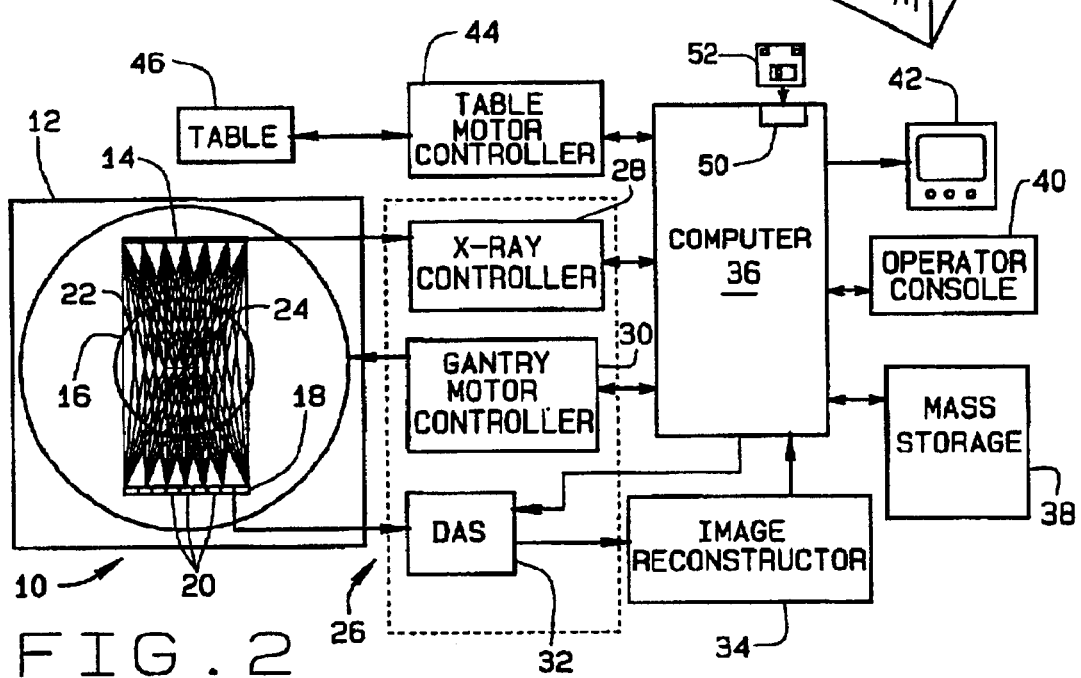
FIG. 2 is a block schematic diagram of the system illustrated in FIG. 2.

Detector array __18__ is formed by a plurality of detector rows (not shown) including a plurality of detector elements __20__ which together sense the projected X-ray beams that pass through an object, such as a medical patient __22__. Each detector element __20__ produces an electrical signal that represents the intensity of an impinging radiation beam and hence the attenuation of the beam as it passes through object or patient 22. During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes an radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
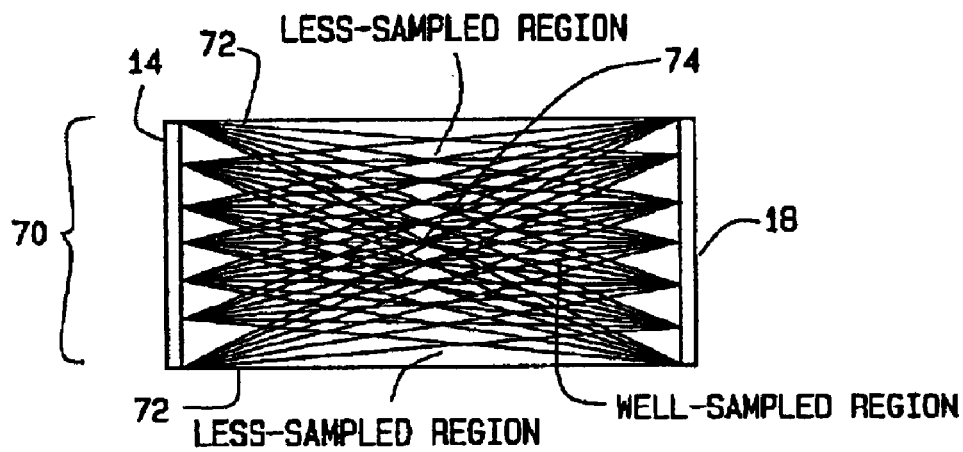
FIG. 3 is a cross-sectional view of an in-homogeneous sampling pattern.

FIG. 3 is a cross-sectional view of an in-homogeneous X-ray sampling pattern acquired in a Z direction, i.e. along patient 22 (shown in FIG. 1) axis. As shown in FIG. 3, a large two-dimensional radiation source 14 is used to cover nearly the entire scan field of view (FOV) 70, and a detector 18, smaller than radiation source 14, is used to collect the x-ray photons emitted from radiation source 14. For example, it is clear that the locations near both FOV edges 72 are sampled less often than a FOV center 74, resulting in an inhomogeneous noise pattern.

Figure 4:
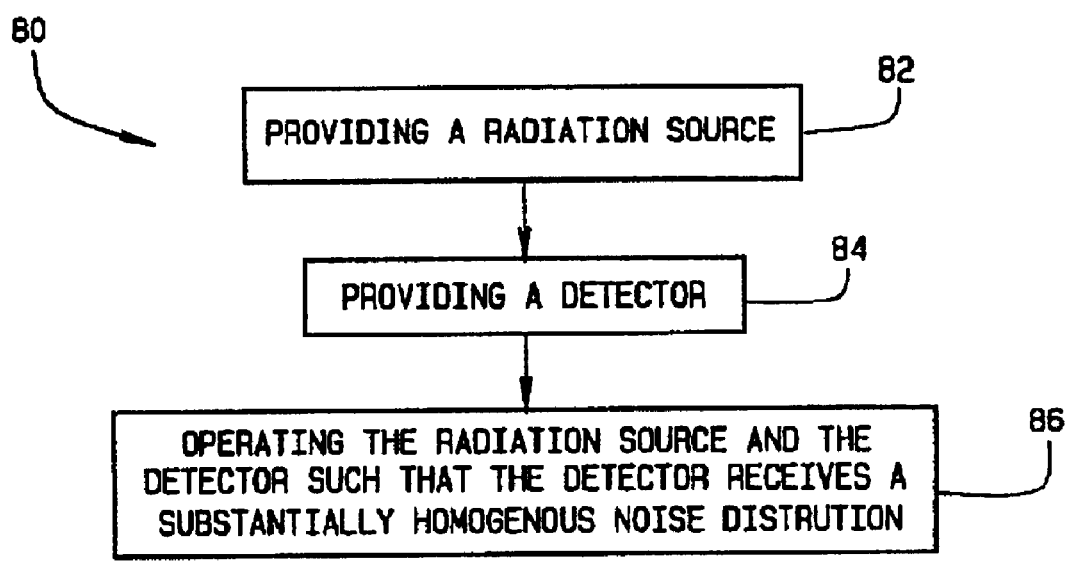
FIG. 4 is a flow diagram of a method for operating a radiation source.

FIG. 4 is a flow diagram of a method 80 for operating a radiation source, such as radiation source 14. Method 80 includes providing 82 a radiation source, providing 84 a detector, such as detector 18, and operating 86 the radiation source and the detector such that the detector receives a substantially homogenous flux and noise distribution.

Figure 5:
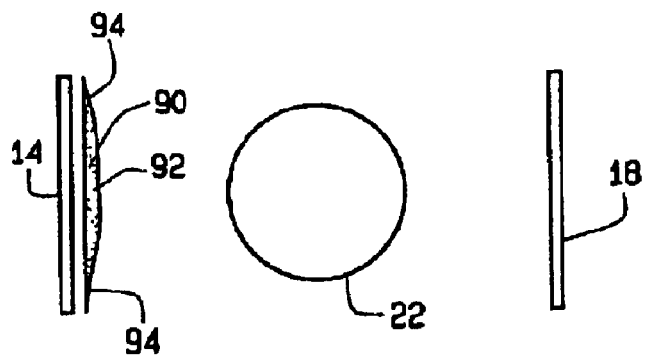
FIG. 5 is a cross-sectional view of a pre-patient filter.

FIG. 5 is a cross-sectional view of an exemplary embodiment of a pre-patient filter 90 used to facilitate a reduction in a inhomogeneous noise pattern. In the exemplary embodiment, pre-patient filter 90 is installed between radiation source 14 and patient 22. In use, pre-patient filter 90 facilitates shaping an X-ray beam intensity such that an increased homogeneous noise distribution is produced. In one embodiment, pre-patient filter 90 is thicker at a filter center 92 and thinner near a filter edge 94. Increased thickness near center 92 facilitates compensating for a greater quantity of samples near FOV center 74 (shown in FIG. 3). Reduced thickness near edge 94 facilitates compensating for a reduced quantity of samples near FOV edge 72 (shown in FIG. 3). Therefore, the total x-ray flux delivered to detector 18 region is approximately homogenous. Pre-patient filter 90 is optimized examining a plurality of flux distributions within FOV 70 (shown in FIG. 3). In one embodiment, this optimization is done using an iterative algorithm. In another embodiment, this optimization is done using an operator selected algorithm.

Figure 6:
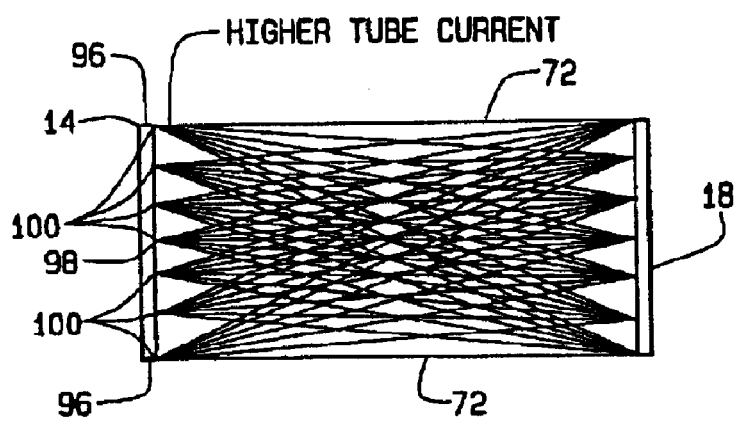
FIG. 6 a cross-sectional view of a spatially homogeneous sampling pattern with variable x-ray tube current.

FIG. 6 is a cross-sectional view of a spatially homogeneous sampling pattern acquired by modulating a radiation source current. In the exemplary embodiment, the radiation source current near a radiation source edge 96 is greater than the radiation source current at a radiation source center 98. For example, an input current to radiation source 14 is not constant, but rather is modulated based on the location of a radiation source spot 100. In use, to compensate for the lack of sampling near FOV edges 72, the radiation source current is highest near radiation source edges 96 and gradually decreases as it approaches radiation source center 98. Similar to the first approach, optimization of the radiation source current as a function of radiation source spot 100 can be carried out by examining the resulting x-ray flux.

Figure 7:
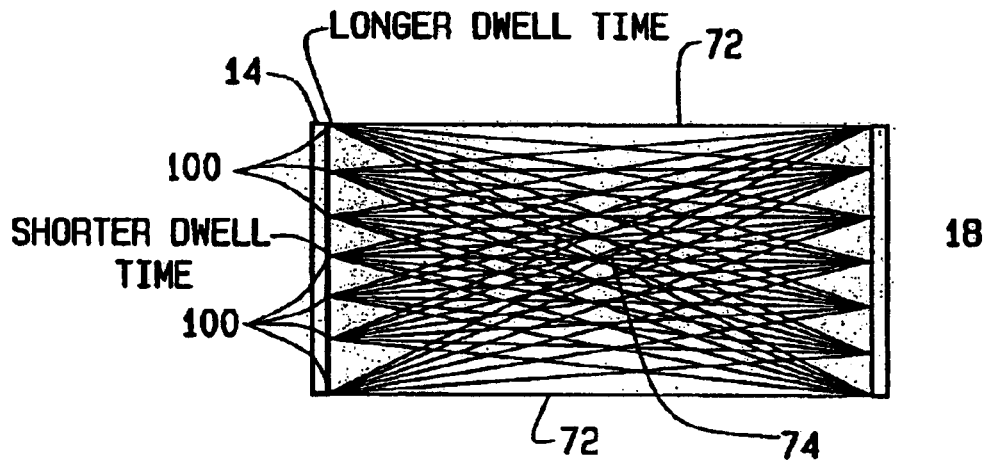
FIG. 7 a cross-sectional view of a spatially homogeneous sampling pattern with inhomogeneous dwelling time.

FIG. 7 is a cross-sectional view of a spatially homogeneous sampling pattern acquired by modulating an x-ray flux distribution. In the exemplary embodiment, modulating an x-ray flux distribution includes changing the dwell time of an electron beam on each source spot 100, while keeping the current to radiation source 14 constant. In use, a longer dwelling time at radiation source spot 100 translates to an increased x-ray flux at the sampling location, similar to the effect obtained by adjusting the radiation source current described previously herein. In one embodiment, a dwell time for x-ray spots 100 near both FOV edges 72 is greater than the dwell time near FOV center 74. In another embodiment, the x-ray dwell time modulation and the radiation source current modulation are combined to generate a homogeneous flux and noise pattern. Modulating the x-ray dwell time and the radiation source current facilitates reducing a requirement on system 10 (shown in FIG. 1) if two modulations need to be carried out separately. For example, if CT system 10 is not able to change the dwell time fast enough to ensure a homogeneous flux file, then a homogeneous noise field can be achieved by partially changing the dwell time and partially changing the radiation source current.

Figure 8:
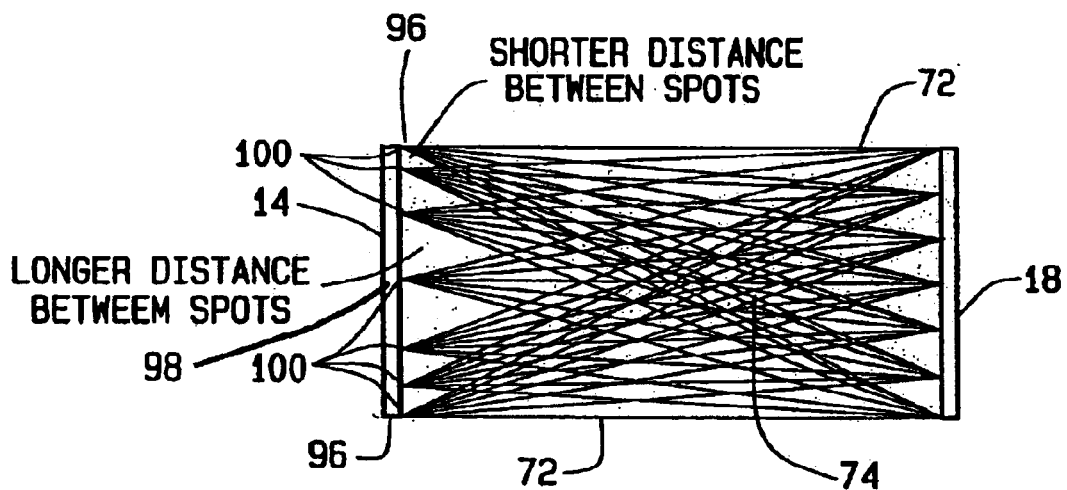
FIG. 8 a cross-sectional view of a spatially inhomogeneous sampling pattern.

FIG. 8 is a cross-sectional view of a homogeneous flux and noise pattern acquired by altering a spatial sampling pattern on source spots 100. For example, assuming a distance between different radiation source spots 100 is constant, a resultant sampling pattern is denser near FOV center 74 and less dense near FOV edges 72. Therefore, and in the exemplary embodiment, the sampling distance between radiation source spots 100 can be modified such that the sampling distances are spaced closer near radiation source edges 96 and further apart near radiation source center 98. Modifying the sampling distances between the radiation source spots 100 facilitates re-normalizing the sampling pattern such that the flux and noise is approximately homogeneous as shown previously in FIG. 7.

In another exemplary embodiment, the methods describe previously herein can be combined to facilitate a reduction in hardware constraints, such as described previously herein. In one embodiment, pre-patient filter 70, the radiation source current modulation, the radiation source dwell time modulation, and a sampling pattern alteration approach can be combined to facilitate a reduction in inhomogeneous noise. In another embodiment, at least two of pre-patient filter 70, the radiation source current modulation, the radiation source dwell time modulation, and a sampling pattern alteration approach can be combined to facilitate a reduction in inhomogeneous noise.

While the invention has been described in terms of various specific embodiments, those skilled in the art will recognize that the invention can be practiced with modification within the spirit and scope of the claims.

What is claimed is:

1. A method for operating a radiation source, said method comprising:
   providing at least one of a line radiation source and a two-dimensional radiation source;
   providing a detector; and
   operating the radiation source and the detector such that the detector receives a substantially homogenous noise distribution.

2. A method in accordance with claim 1 further comprising operating the radiation source such that at least one of an inverted-cone beam geometry and a non-inverted cone beam geometry is received by the detector.

3. A method in accordance with claim 1 further comprising installing a filter between the radiation source and an object of interest such that an x-ray flux delivered to a plurality of regions in a field of view is approximately homogeneous.

4. A method in accordance with claim 1 further comprising modulating a radiation source current such that the radiation source current near an edge of the radiation source is greater than the radiation current at a center of the radiation source.

5. A method in accordance with claim 1 further comprising modulating a dwell time of an electron beam emitted from the radiation source such that a dwell time at an X-ray spot near an edge of a field of view is greater than the dwell time at an X-ray spot near a center of the field of view.

6. A method in accordance with claim 1 further comprising modifying a sampling distance between a plurality of x-ray spots such that the spots near an edge of the radiation source are spaced closer than the spots near a center of the radiation source.

7. A method for operating a radiation source on a scanning imaging system, wherein said imaging system comprises a radiation source, a detector, and a filter between said radiation source and said detector, said method comprising:
   operating the radiation source such that at least one of an inverted-cone beam geometry and a non-inverted cone beam geometry is received by the detector;
   modulating the radiation source current such that the radiation source current near an edge of the radiation source is greater than the radiation source current at a center of the radiation source; and
   modulating a dwell time of an electron beam emitted from the radiation source such that a dwell time at an X-ray spot near an edge of the field of view is greater than the dwell time at an X-ray spot near the center of the field of view.

8. A method in accordance with claim 7 wherein said operating the radiation source such that at least one of an inverted-cone beam geometry and a non-inverted cone beam geometry is received by the detector comprises operating at least one of a line radiation source and a two-dimensional radiation source.

9. A method in accordance with claim 7 further comprising modifying a sampling distance between a plurality of X-ray spots such that the spots near an edge of the radiation source are spaced closer than the spots near a center of the radiation source such that the detector receives a substantially homogenous noise distribution.

10. A computer operating a radiation source installed on a scanning imaging system, wherein said imaging system comprises a at least one of a line radiation source and a two-dimensional radiation source and a detector, said computer programmed to operate the at least one of a line radiation source and a two-dimensional radiation source and the detector such that the detector receives a substantially homogenous noise distribution.

11. A computer in accordance with claim 10 further programmed to operate the radiation source such that at least one of an inverted-cone beam geometry and a non-inverted cone beam geometry is received by the detector.

12. A computer in accordance with claim 10 further programmed to operate the imaging system, wherein said imaging system further comprises a filter installed between the radiation source and an object of interest such that an x-ray flux delivered to a plurality of regions in a field of view is approximately homogeneous.

13. A computer in accordance with claim 10 further programmed to modulate a radiation source current such that the radiation source current near an edge of the radiation source is greater than the radiation current at a center of the radiation source.

14. A computer in accordance with claim 10 further programmed to modulate a dwell time of an electron beam emitted from the radiation source such that a dwell time at an X-ray spot near an edge of a field of view is greater than the dwell time at an X-ray spot near the center of the field of view.

15. A computer in accordance with claim 10 further programmed to modify a sampling distance between a plurality of x-ray spots such that the spots near an edge of the radiation source are spaced closer than the spots near a center of the radiation source.

16. A computed tomographic CT imaging system for operating a radiation source, said CT system comprising:
   a radiation source;
   a detector array; and
   a computer coupled to said detector array and said radiation source, said computer configured to operate said radiation source such that at least one of an inverted-cone beam geometry and a non-inverted cone beam geometry is received by said detector array, and wherein said computer is further configured to modulate a radiation source current such that the radiation source current near an edge of said radiation source is greater than the radiation current at a center of said radiation source.

17. A CT system in accordance with claim 16, wherein said radiation source comprises at least one of a line radiation source and a two-dimensional radiation source.

18. A CT system in accordance with claim 16, wherein said CT imaging system further comprises a filter installed between the radiation source and an object of interest such that an x-ray flux delivered to a plurality of regions in a field of view is approximately homogeneous.

19. A computed tomographic CT imaging system for operating a radiation source, said CT system comprising:

a radiation source;

a detector array; and a computer coupled to said detector array and said radiation source, said computer configured to operate said radiation source such that at least one of an inverted-cone beam geometry and a non-inverted cone beam geometry is received by said detector array, and wherein said computer is further configured to modulate a dwell time of an electron beam emitted from said radiation source such that a dwell time at an X-ray spot near an edge of a field of view is greater than a dwell time at an X-ray spot near the center of the field of view.

20. A CT system in accordance with claim 19, wherein said radiation source comprises at least one of a line radiation source and a two-dimensional radiation source.

21. A CT system in accordance with claim 19, wherein said CT imaging system further comprises a filter installed between the radiation source and an object of interest such that an x-ray flux delivered to a plurality of regions in a field of view is approximately homogeneous.

22. A computed tomographic CT imaging system for operating a radiation source, said CT system comprising:

a radiation source;

a detector array; and a computer coupled to said detector array and said radiation source, said computer configured to operate said radiation source such that at least one of an inverted-cone beam geometry and a non-inverted cone beam geometry is received by said detector array, and wherein said computer is further configured to modify a sampling distance between a plurality of x-ray spots such that the spots near an edge of said radiation source are spaced closer than the spots near a center of said radiation source.

23. A CT system in accordance with claim 22, wherein said radiation source comprises at least one of a line radiation source and a two-dimensional radiation source.

24. A CT system in accordance with claim 22, wherein said CT imaging system further comprises a filter installed between the radiation source and an object of interest such that an x-ray flux delivered to a plurality of regions in a field of view is approximately homogeneous.

\* \* \* \* \*